US008357720B2

(12) United States Patent
Weissbach et al.

(10) Patent No.: US 8,357,720 B2
(45) Date of Patent: Jan. 22, 2013

(54) TREATMENT OR PREVENTION OF CANCER AND PRECANCEROUS DISORDERS

(75) Inventors: Herbert Weissbach, Boynton Beach, FL (US); Lionel Resnick, Weston, FL (US); David Binninger, Delray Beach, FL (US)

(73) Assignee: Florida Atlantic University, Boca Raton, FL (US)

( * ) Notice: Subject to any disclaimer, the term of this patent is extended or adjusted under 35 U.S.C. 154(b) by 169 days.

(21) Appl. No.: 12/557,022

(22) Filed: Sep. 10, 2009

(65) Prior Publication Data
US 2010/0069331 A1    Mar. 18, 2010

Related U.S. Application Data

(63) Continuation-in-part of application No. 11/925,283, filed on Oct. 26, 2007, which is a continuation-in-part of application No. 11/388,248, filed on Mar. 23, 2006, now Pat. No. 8,258,181.

(60) Provisional application No. 60/664,383, filed on Mar. 23, 2005.

(51) Int. Cl.
*A61K 31/255* (2006.01)
*A61K 33/40* (2006.01)

(52) U.S. Cl. ........ 514/518; 514/18.7; 514/516; 424/616

(58) Field of Classification Search ................. 514/18.7, 514/516, 518; 424/616
See application file for complete search history.

(56) References Cited

U.S. PATENT DOCUMENTS

| | | | | |
|---|---|---|---|---|
| 4,732,864 | A | | 3/1988 | Tolman |
| 5,204,116 | A | * | 4/1993 | Edgren et al. ............... 424/473 |
| 5,338,550 | A | * | 8/1994 | Edgren et al. ............... 424/473 |
| 5,370,870 | A | * | 12/1994 | Wong ............................ 424/85.1 |
| 5,942,520 | A | * | 8/1999 | Pamukcu et al. ............. 514/293 |
| 5,955,504 | A | * | 9/1999 | Wechter et al. ............... 514/568 |
| 6,258,845 | B1 | * | 7/2001 | Gerner et al. ................. 514/544 |
| 6,413,937 | B1 | * | 7/2002 | Clynes .......................... 514/34 |
| 6,472,378 | B2 | * | 10/2002 | von Borstel .................. 514/50 |
| 2003/0143165 | A1 | * | 7/2003 | Evans et al. .................. 424/59 |
| 2003/0232767 | A1 | * | 12/2003 | Agrawal et al. .............. 514/44 |
| 2004/0137077 | A1 | | 7/2004 | Ancira et al. |
| 2004/0143016 | A1 | | 7/2004 | Weissbach et al. |
| 2004/0234450 | A1 | * | 11/2004 | Howes ....................... 424/1.11 |
| 2004/0234625 | A1 | * | 11/2004 | Burstein .................... 424/666 |
| 2006/0166947 | A1 | | 7/2006 | Anderson et al. |

FOREIGN PATENT DOCUMENTS

| | | | |
|---|---|---|---|
| EP | 0270316 A2 | * | 6/1988 |
| WO | 0050448 | | 8/2000 |
| WO | WO-02/067987 A2 | * | 9/2002 |
| WO | 2006/102439 A2 | | 9/2006 |

OTHER PUBLICATIONS

Giardello, "Sulindac and Polyp Regression", 1994, Cancer and Metastasis Reviews, vol. 13, pp. 279-283.*

Matsubara, J., Experientia Supplementum, 1987, vol. 52, pp. 603-613, especially Abstract, p. 610.

T.T. Jiang,. S. I, Brown J.H. Kim, "Combined Effect of Arsenic Trioxide and Sulindac Sulfide in A549 Human Lung Cancer Cells In Vitro", J. Exp. Clin. Cancer Res., 23, 2, 2004, pp. 259-262.

Minami et al "Sulindac Enhances the Proteasome Inhibitor Bortezomib-Mediated Oxidative Stress and Anticancer Activity". Ciin. Cancer Res., (2005), vol. 11, No. 14, pp. 5248-5256.

Giardello, et al. "Primary Chemoprevention of Familial Adenomatous Polyposis with Sulindac: More Questions than Answers", Gastroenteroogy, (2002), vol. 123, pp. 379-387.

Matsumoto, et al. Effect of the non-steroidal anti-inflammatory drug sulindac on colorectal adenoma of uncolectomize familial andenomatous polyposis, Journal of Gastroenterology and Hepatology, (2006), vol. 21 251-257.

Arber, et al "Sporadic adenomatous polyp regression with exisulind is effective but toxic: a randomised, double blind, placebo controlled, dose-response study", Downloaded on Sep. 6, 2006 from gut.bmj-journals.com, GUT 2006, vol. 55, pp. 367-373.

Piazza, et al. "Sulindac Sulfone Inhibits Azoxymethane-induced Colon Carcenogenesis in Rats without reducing Prostaglandin Levels", Cancer Research, (1997), vol. 57, pp. 2909-2915.

Rao at al, "Chemoprevention of Colon Carcenogenesis by Sulindac, a Nonsteroidal Antiflammator Agent", Cancer-Research, (1995), vol. 55, pp. 1464-1472.

Shiff, et al."Sulindac, Sulfide, an Aspirin-like Compound, Inhibits Proliferation, Causes Cell Cycle Quiescence. and Induces Apoptosis in HT-29 Colon Adenocarcinoma Cells", J Clin. Inves., (1995). vol. 96. pp. 491-503.

Hileman et al "Intrinsic oxidative stress in cancer cells; a biochemical basis for therapeutic selectivity", Cancer Chemother Pharmacol, (2004), vol. 53, pp. 209-219.

Rice, et al. "Sulindac metabolites induce caspase- and proteasome-dependent degradation of beta-catenin protein in human colon cancer cells", Molecular Cancer Therapeutcs, (2003) pp. 885-892.

Sinicrope et al. Sulindac sulfide-induced apoptosis is enhanced by a small-molecule Bcl-2 inhibitor and by TRAIL in human colon cancer cells overexpressing Bcl-2, Mol. Cancer Ther., (2005). vol. 4, No. 10, pp. 1475-1483.

Jung et al. "Mechanisms of Sulidac-induced apoptosis and cell cycle arrest", Cancer Letters, (2005), vol. 219, pp. 15-25.

Yasui et al."Combination of Tumor Necrosis Factor-alpha with Sulindac Augments its Apoptotic Potential and Suppress Tumor Growth of Human Carcinoma Cells in Nude Mice", Cancer, (2003), vol. 97 No. 6, pgs.

Fernandes et al. "Ther Metabolism of Sulindac Enhances its Scavenging Activity Against Reactive Oxygen and Nitrogen Species", Free Radical Biology & Medicine, (2003), vol. 35, No. 9, pp. 1008-1017.

Costa et al. "Hydrogen peroxide scavenging activity by non-steroidal anti-inflammatory drugs", Life Science, (2005), vol. 76, pp. 2841-28242.

(Continued)

*Primary Examiner* — Ali Soroush
(74) *Attorney, Agent, or Firm* — Novak Druce Quigg LLP

(57) ABSTRACT

The NSAID, sulindac and/or its metabolites and derivatives, in combination with an agent that generates or induces reactive oxygen species (ROS), significantly enhances the killing of abnormal cells but does not affect normal cells. This effect occurs at concentrations of each compound that individually have little or no activity directed against the abnormal cells.

4 Claims, 6 Drawing Sheets

OTHER PUBLICATIONS

Zhang et al. "The Chemopreventive Agent Sulindac Attenuates Expression of the Antiapoptotic Protein Survivin in Colorectal Carcinoma Cells". The Journal of Pharmacology and Experimental Therapeutics, (2004). vol. 308, No. 2, pp. 434-437.

Clinical Cancer Research Abstract. AACR Special Conference Feb. 8-12, 2006. Fig. 5 Combination therapy-medicated oxidative DNA damage in DLD-1 cells.

O'Connor Robert et al, "Increased anti-tumour efficacy of doxorubicin when combined with sulindac in a xenograft model of an MRP-1-positive human lung cancer": Anticancer Research, The National Institute for Cellular Biotechnology, Ireland, (2004), vol. 24, pp. 457-464, XP008125995.

Kim Hak Ryul et al, "Combination of arsenic trioxide with sulindac augments cell death and induced apoptosis via activation of caspase cascade in NCI-H157 human lung carcinoma cells": Proceedings of the American Association for Cancer Research; Rep. of Korea, (2004), vol. 45, p. 1227, XP008125990.

Supplementary European Search Report; EP 06 74 8561, dated Sep. 1, 2010.

* cited by examiner

A.

B.

A.

B.

A. A459 cells:

DCA (10 mM):        −           −           +           +
Sulindac (500 µM):  −           +           −           +

B. SCC25 cells:

DCA (10 mM):        −           −           +           +
Sulindac (100 µM):  −           +           −           +

TREATMENT OR PREVENTION OF CANCER AND PRECANCEROUS DISORDERS

CROSS REFERENCE TO PRIOR APPLICATIONS

The present application is continuation-in-part (CIP) of application Ser. No. 11/925,283 filed Oct. 26, 2007, which is a continuation-in-part (CIP) of application Ser. No. 11/388,248 filed Mar. 23, 2006, which claims priority to U.S. provisional application No. 60/664,383 filed Mar. 23, 2005, all of which are incorporated herein by reference in their entireties.

FIELD OF THE INVENTION

Compositions for treating cancer and methods of treating thereof. In particular, sulindac and/or its metabolites and derivatives, in R- or S-epimeric form with or without an agent that generates reactive oxygen species (ROS), significantly enhances the killing of cancer cells but does not affect normal cells.

BACKGROUND OF THE INVENTION

Skin cancer is the most common form of cancer seen in the world. The two most common types of non-melanoma skin cancer include basal cell carcinoma (BCC) and squamous cell carcinoma (SCC). One in five Americans will develop some form of skin cancer at some point in their lives, and it is estimated that over one million Americans will develop skin cancer each year.

Sun exposure has been implicated in the etiology of BCC and SCC. The epidemic rise in the rate of these cancers is directly related to increases in our population's outdoor activities and the desire for a "tanned" skin appearance. Premalignant actinic keratoses are common skin growths induced by solar exposure that have the potential for developing into SCC in upwards of 20% of cases. They often appear on the skin years before the development of cutaneous carcinomas.

It is considered a standard of care to remove as many skin cancers and actinic keratoses as possible with the least amount of discomfort, inconvenience and trauma (morbidity), for the patient. Destruction using liquid nitrogen or electrodessication and curettage are effective in removing a majority of skin cancers and actinic keratoses. However, these treatments may not be practical for certain skin cancers located on the face and extremities. Surgical removal of skin cancers and actinic keratoses is not always possible or desirable. Surgery is not practical when many small actinic keratoses are present, and the scarring produced by surgery is generally unacceptable for exposed, relatively visible areas of the skin. Furthermore, it is believed that, in the early stages of their development, many skin cancers and actinic keratoses are so small that it would be difficult or impossible to remove surgically because they are not visible to the eye. Surgery, while necessary for the welfare of the patient, may place the patient at risk and ultimately jeopardize their health if the cancer is located adjacent to certain vital areas, such as the eye. In addition, surgery may lead to a poor cosmetic effect and leave the patient visibly deformed.

Topically applied, chemical agents such as 5-fluorouracil (5-FU, Efudex, Fluoroplex), masoprocol (Actinex), imiquimod (Aldara), and diclofenac (Solaraze) have been approved to eradicate actinic keratoses. While 5-FU has demonstrated efficacy for this purpose, it has been found to cause pain, itching, skin inflammation, ulceration and cosmetic disfigurement often so severe that patients hide at home and stop using it, thus making its therapeutic use unacceptable to many individuals. These effects also preclude the use of 5-FU over large areas of the skin to treat incipient and/or microscopic actinic keratoses. Masoprocol was removed from the US market in 1996 after it was found to have a high incidence of contact sensitivity and allergic reactions. Imiquimod has a relatively good cosmetic effect when treating actinic keratoses but is very expensive for use in large areas of the skin and its packaging in pouches has not been well received by many patients. The Food and Drug Administration recently approved imiquimod for the treatment of BCC. However, this indication excludes treatment of BCC that occurs on the face. Diclofenac is a non-steroidal anti-inflammatory drug (NSAID) used to treat actinic keratoses. It has very modest effects and removal of the actinic keratoses may not be evident until months after treatment ends. However, it causes less irritation than 5-FU and imiquimod and may be useful for some people.

There are several newer therapeutic approaches directed against actinic keratoses that are in clinical trials such as the use of photodynamic therapy (PDT) with aminolevulinic acid. This therapy is a two-step treatment administered over a two-day period. First, the aminolevulinic acid is place over the lesion and on the next day, a blue light is used to activate the drug. However, this treatment is expensive, needs to be done at the doctor's office, is used only for thin lesions, and is not very effective.

SUMMARY

This Summary is provided to present a summary of the invention to briefly indicate the nature and substance of the invention. It is submitted with the understanding that it will not be used to interpret or limit the scope or meaning of the claims.

Compositions for the treatment of diseases or disorders associated with abnormal cells, or abnormal cell proliferation comprises sulindac and an agent which inducers the production or generation of reaction oxygen intermediate species (ROS). Normal cells are not affected by the treatment.

Methods for the treatment of abnormal cells or abnormal cell proliferative diseases such as for example, cancer comprise the administration to a patient of the composition comprising sulindac and one or more reactive oxygen species inducers, such as for example, dichloroacetic acid.

The sulindac can be an epimer of sulindac, such as for example R- or S- or mixtures thereof, sulindac derivatives, analogs, variants and derivatives thereof.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which.

DETAILED DESCRIPTION

Figure 1A:
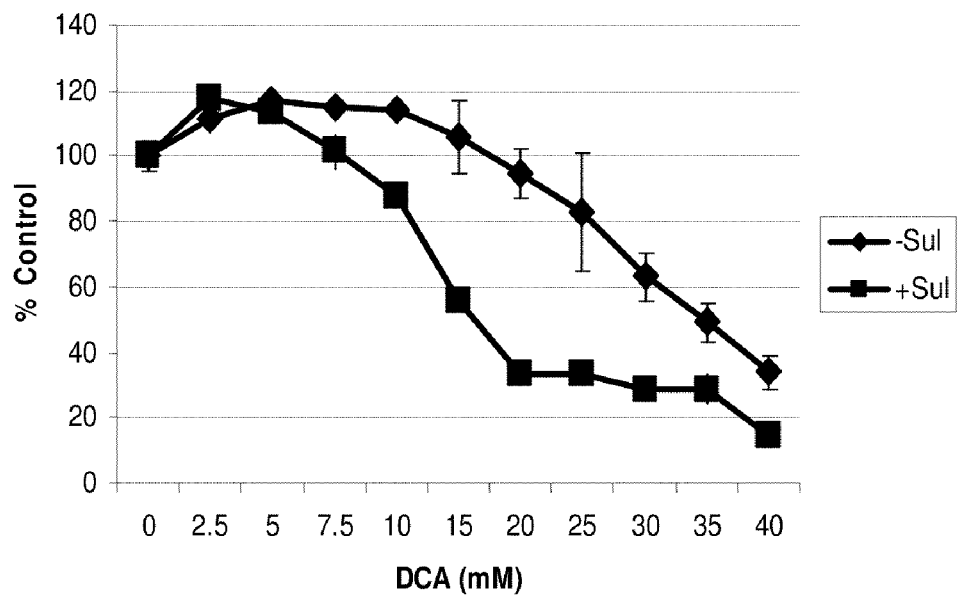
FIGS. 1A-1D shows the synergistic effect of sulindac and DCA drug combination during selective killing of cancer cells. The A549 lung and SCC25 skin carcinoma cells, normal lung cells, and keratinocytes were treated with the indicated concentrations of DCA in the presence or absence of sulindac for 48 hours. The cell viability was monitored by MTS assay as mentioned in the Materials and Methods. The cell viability is expressed as % of control (cells not treated with sulindac). Error bars are standard error of the mean (SEM) expressed as % of the mean value of quadruplicates from a representative experiment. Inhibition of cancer cell growth occurred in a dose dependent manner during combination treatment of DCA and sulindac in A549 cells (FIG. 1A) and in SCC25 cells (FIG. 1B). No significant change in cell viability was observed with normal lung cells (FIG. 1C) and human keratinocytes (Figure D). solid diamonds—no sulindac; solid squares—plus sulindac.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Treatment or prevention of a cancerous or precancerous disorder in humans or animals in need of such treatment or prevention is provided by methods and combinations using two or more components.

DEFINITIONS

In accordance with the present invention and as used herein, the following terms are defined with the following meanings, unless explicitly stated otherwise.

As used herein, "a", "an," and "the" include plural references unless the context clearly dictates otherwise.

As used herein, "sulindac" refers to sulindac, both R- and S-epimers, sulindac derivatives, metabolites, analogues and variants thereof. Examples of sulindac metabolites include sulindac sulfide, sulindac sulfone.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head & neck, kidney, lung, non-small cell lung, melanoma, mesothelioma, ovary, sarcoma, stomach, uterus and Medulloblastoma. The term "cancer" includes any cancer arising from a variety of chemical, physical, infectious organism cancer causing agents. For example, hepatitis B virus, hepatitis C virus, human papillomaviruses; sun; lead and lead compounds, X-rays, compounds found in grilled meats, and a host of substances used in textile dyes, paints and inks. Further details of cancer causing agents are listed in *The Report on Carcinogens*, Eleventh Edition. Federal law requires the Secretary of the Department of Health and Human Services to publish the report every two years.

Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

The term "sarcoma" generally refers to a tumor which is made up of a substance like the embryonic connective tissue and is generally composed of closely packed cells embedded in a fibrillar or homogeneous substance. Examples of sarcomas which can be treated with the compositions and optionally a potentiator and/or chemotherapeutic agent include, but not limited to a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the compositions and optionally a potentiator and/or another chemotherapeutic agent include but not limited to, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the compositions and optionally a potentiator and/or a chemotherapeutic agent include but not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Diagnostic" or "diagnosed" means identifying the presence or nature of a pathologic condition or a patient susceptible to a disease. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The treatment of neoplastic disease, cancer, or neoplastic cells, refers to an amount of the composition, described throughout the specification and in the Examples which follow, capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention of tumor cell infiltration into peripheral organs; (6) inhibition, including (i) reduction, (ii) slowing down or (iii) complete prevention of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder.

The terms "dosing" and "treatment" as used herein refer to any process, action, application, therapy or the like, wherein a subject, particularly a human being, is rendered medical aid with the object of improving the subject's condition, either directly or indirectly.

The term "therapeutic compound" as used herein refers to a compound useful in the prophylaxis or treatment of cancer.

The term "therapeutic combination" as used herein refers to the administered therapeutic compounds when administered in combination therapy, and to any pharmaceutically acceptable carriers used to provide dosage forms such that the beneficial effect of each therapeutic compound is realized by the subject at the desired time, whether the compounds are administered substantially simultaneously, or sequentially.

The compounds of the invention encompass various isomeric forms. Such isomers include, e.g., stereoisomers, e.g., chiral compounds, e.g., diastereomers and enantiomers.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not minor images of one another.

The term "enantiomers" refers to two stereoisomers of a compound which are non-superimposable minor images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space. Diastereoisomers that have the opposite configuration at only one of two or more tetrahedral stereogenic centres present in the respective molecular entities are known as "epimers." Thus, when used herein "sulindac" or variants, derivatives or oxides thereof, includes epimeric and enantiomeric molecules.

Furthermore the indication of configuration across a carbon-carbon double bond can be "Z" referring to what is often referred to as a "cis" (same side) conformation whereas "E" refers to what is often referred to as a "trans" (opposite side) conformation. Regardless, both configurations, cis/trans and/or Z/E are contemplated for the compounds for use in the present invention.

With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

Compositions

The present invention provides a composition comprising sulindac, epimers of sulindac, metabolites, derivatives, analogs, and variants thereof, in the prevention and treatment of cancer in a patient.

In a preferred embodiment, the composition comprises a therapeutically effective dose of sulindac, epimers of sulindac, metabolites, derivatives, analogs, and variants thereof and an agent which induces reactive oxygen species in a cell, tissue or in vivo.

In a preferred embodiment, a composition comprises at least about 10% (v/v) sulindac; preferably the composition comprises about 50% (v/v) sulindac; preferably the composition comprises about 75% (v/v) sulindac; preferably, the composition comprises about 90% (v/v) sulindac; more preferably, the composition comprises about 95%, 96%, 97%, 98%, 99%, 99.9% (v/v) sulindac.

In another preferred embodiment, the agent which induces reactive oxygen intermediates is inclusive of any such agent, for example, dichloroacetic acid, bisphenol A (BPA), tetramethylrhodamine derivatives, N-(4-hydroxyphenyl)retinamide (HPR), dithiophene, menadione (vitamin K3) X radiation, or phytol (3,7,11,15-tetramethyl-2-hexadecene-1-ol).

In a preferred embodiment, the agent is dichloroacetic acid (DCA).

In another preferred embodiment, prevention or treatment of cancer or abnormal cells and disorders thereof comprises administering to a patient a therapeutically effective amount of the sulindac composition. The administration can be via any acceptable route such as, for example, intra-venously, intra-peritoneally, intra-muscularly, subcutaneously, orally, topically, via inhalation.

Cancer or neoplasm or malignant tumors in mammals, include, but not limited to: leukemias, lymphomas, melanomas, carcinomas and sarcomas. Examples of cancers are cancer of the brain, breast, pancreas, cervix, colon, head & neck, kidney, lung, non-small cell lung, melanoma, mesothelioma, ovary, sarcoma, stomach, uterus and Medulloblastoma. The term "cancer" includes any cancer or abnormal cell arising from a variety of genetic, chemical, physical, infectious organism cancer causing agents.

In another preferred embodiment, treatment with a therapeutically effective amount of sulindac, its derivatives, metabolites and variants thereof, optionally comprises a combination of two or more agents. The first agent is R-sulindac or S-sulindac or their metabolites or derivatives. The second agent is an oxidizing agent or agent that leads to the generation of ROS, e.g. DCA. Besides being useful for human treatment, the present invention is also useful for veterinary treatment of companion animals, exotic animals and farm animals, including mammals, rodents, and the like. More preferred animals include horses, dogs, and cats.

The enhanced cancer cell killing effects of the combination of sulindac and an oxidizing agent has not been previously described.

The experimental results revealed that sulindac had a dual effect, in a sense a reverse effect, such that normal cells were protected but cancer cells were killed. This effect is specific to sulindac and is not seen with other NSAIDs. The mechanism of action suggests that cancer cells or highly proliferating cells, become more sensitive to the effects of ROS. Normal cells or cells that are not in a hyper-proliferative state are protected and become less sensitive to the effects of ROS. This dual effect of sulindac was totally unexpected and surprising. Details are provided in the examples which follow.

Polyps of the colon are precancerous growths that if left untreated can progress to adenocarcinoma of the colon in a significant number of patients. Once a polyp is detected in the colon, surgical intervention is recommended to remove or destroy the lesion. However, the need exists to develop chemoprevention strategies for patients that cannot tolerate polypectomy or who are unwilling or unable to have a protectomy. Sulindac has been known as an anti-inflammatory and analgesic drug since the early 1970's. It is claimed in U.S. Pat. No. 3,654,349 issued to Shen et al in 1972, and commercialized by Merck under the trade name Clinoril. Several NSAIDs, originally developed to treat arthritis, such as sulindac have shown effectiveness in inhibiting and eliminating colonic polyps and in some cases, adenocarcinoma of the colon. Polyps virtually disappear when the NSAID that the patient takes is sulindac. However, the prophylactic use of currently available NSAIDs, even in polyposis syndrome patients, is marked by severe side reactions that include gastrointestinal irritations and ulcerations. Once sulindac treatment is terminated due to such complications, the polyps can return, particularly in polyposis syndrome patients.

The compounds used in the treatment of this invention are effective on precancerous and cancerous lesions either because they are active themselves or because they are metabolized to active derivatives. In a preferred embodiment, a structurally related compound can be substituted for both compounds e.g. Sulindac, DCA and peroxides).

Oxidizing groups contemplated for use in accordance with the present invention include peroxides, nitrates, nitrites, perchlorates, chlorates, chlorites, hypochlorite, dichromates, permanganates, and persulfates. Use of other electron accepting compounds including those not containing oxygen is within the scope of the invention as well. Bromine is an example of such a compound. Use of oxidizing agents or compounds that cause cells to produce ROS such as retinoic acid (and its derivatives), K antimonyl tartrate, doxorubicin, imexon, and bortezomib are within the scope of this invention.

Non-limiting examples of agents which generate or induce ROS comprise: dichloroacetic acid, bisphenol A (BPA), tetramethylrhodamine derivatives, N-(4-hydroxyphenyl) retinamide (HPR), dithiophene, menadione (vitamin $K_3$) X radiation, or phytol (3,7,11,15-tetramethyl-2-hexadecene-1-ol).

Examples of peroxide compounds include, without limitation, hydrogen peroxide; organic peroxides; inorganic peroxides such as sodium peroxyborate tetrahydrate (sodium perborate tetrahydrate) and calcium peroxide; peroxide complexes such as urea hydrogen peroxide, and superoxide salts such as sodium superoxide. In aqueous solution, the superoxide free radical ($O_2^*$) dismutates (via reaction with its conjugate acid, the perhydroxyl free radical) to form hydrogen peroxide, and in biological systems the enzyme superoxide dismutase accelerates dismutation. Examples of organic peroxides include hydroperoxides (ROOH) such as lipid hydroperoxides, and internal peroxides such as artemisinin and its derivatives (an endoperoxide used in the treatment of malaria). Elf Atochem, Inc. (Philadelphia, Pa.) is a source of many organic peroxide compounds. Hydrogen peroxide of high purity can be obtained from Solvay Interox and other commercial sources. 1-Hydroperoxycyclohexyl-1-hydroxy cyclohexyl peroxide and tert-Butyl hydroperoxide can be obtained from Pfaltz and Bauer. Artemisinin can be obtained from Aldrich Chemical Company and Sigma Chemical Company. Sodium peroxyborate tetrahydrate can be obtained from Alfa Johnson Matthey and from Fluka Chemika Biochemika. Urea hydrogen peroxide is available from Aldrich Chemical Company. Methods for the preparation of fatty acid hydroperoxides (such as, for example, linolenic acid hydroperoxide, arachidonic acid hydroperoxide, and docosahexaenoic acid hydroperoxide) and of other lipid hydroperoxides (such as, for example, cholesterol hydroperoxide, cholesteryl linoleate hydroperoxide, trilinolein hydroperoxide, phosphatidylcholine hydroperoxide, and phosphatidylethanolamine hydroperoxide) are well known to those familiar with the art. Many other peroxide compounds are available from commercial sources, and include 3-chloroperoxybenzoic acid, 1,1-bis(tert-butylperoxy)cyclohexane, peracetic acid, monoperoxyphthalic acid, tert-butyl peroxide, 2,5,bis(tert-butylperoxy)-2,5-dimethyl-3-hexyne, cumene hydroperoxide, 2,5-bis(tert-butylperoxy)-2,5-dimethylhexane, lauroyl peroxide, benzoyl peroxide, dicumyl peroxide, 2,5-dihydroperoxy-2,5-dimethylhexane, tert-butyl peracetate, tert-amyl hydroperoxide, diisononanoyl peroxide, decanoyl peroxide, succinic acid peroxide, 2,4-pentanedione peroxide, di-tert-butyl peroxide, tert-butyl cumyl peroxide, bis(t-butylperoxy)diisopropylbenzene, and 1-((hydroperoxycyclohexyl)dioxy)-cyclohexanol. As used in this specification, and in the claims appended hereto, the term peroxide or peroxide compound is meant to be inclusive of hydrogen peroxide, inorganic peroxides, organic peroxides, peroxide complexes, other compounds containing the peroxy (peroxy) —O—O— moiety, superoxides, and peroxide precursor compounds which generate peroxide species in situ. Examples of organic peroxides include hydroperoxides, internal peroxides, endoperoxides, diacyl peroxides, ketone peroxides, peroxydicarbonates, peroxyesters, dialkyl peroxides, peroxyketals, and peroxyacids. Methods for the synthesis of organic peroxides are well known to those familiar with the art can be used in accordance with the present invention. Use of chromic acid, iodine, oxygen, ozone, peroxycarboxylic acids, permanganate, peroxyethanoic acid and peroxybenzoic acid is also contemplated. The primary effect of the oxidizing agent is to kill cellular material by binding a free radical molecule with the biological material and oxidizing the biological material. Therefore, it is also believed that any biologically active free radical, such as a heavy metal radical, may be effective.

The concentration of the sulindac in the topical formulation can range from about 0.01% to 99.9%. The DCA can be in any amount which is sufficient to induce reactive oxygen species intracellularly or extracellularly, in vitro or in vivo. The carrier may further include humectants, fragrances, colors, thickeners, lubricants and preservatives, as is well known in the art. One particularly preferred humectant comprises a collagen derived material such as collagen laurate or the like. In some instances, the carrier may simply comprise water, whereas in other instances it may be a lotion based carrier and may typically include ingredients such as glycerine, propylene glycol, methyl and/or propyl paraben, hydroxyalkyl cellulose and the like. In one preferred embodiment, the carrier may comprise a hypo-allergenic, high lipid, cream based carrier.

Sulindac has been particularly well received among the NSAIDs for gastrointestinal polyp treatment. Sulindac is a sulfoxide compound that itself is believed to be inactive as an anti-arthritic agent. The sulfoxide is known to be converted by liver and other tissues to the corresponding sulfide, which is acknowledged to be the active moiety as a prostaglandin inhibitor. Recently, this conversion has been shown to be catalyzed by methionine sulfoxide reductase (MsrA). The sulfide, however, is associated with the side effects of conventional NSAIDs. Sulindac appears to be metabolized to sulindac sulfone by as yet unknown reactions. Sulindac sulfone is not an inhibitor of prostaglandin synthesis but has apoptotic activity against a wide array of cancer cells. The sulfone is currently being evaluated in Phase 2-3 clinical trials as therapy for multiple different types of cancers.

ROS generating agent concentrations used in various methods according to the present invention can range from about 0.001% to 50% and can be varied according to exposure time. Preferably, the exposure time is less than 45 minutes, more preferably less than 15 minutes, and most preferably no more than 10 minutes. If the agent is delivered on a strip or in a gel or other matrix, the exposure time may be very long and indefinite. One method utilizes a DCA/adhesive mixture to provide a longer exposure. The composition can comprise the ROS generating agent or the agent may be administered prior to, during or after administration of sulindac.

When administered as a combination, the therapeutic agents can be formulated as separate compositions which are given at the same time or different times, or the therapeutic agents can be given as a single composition. The two components may be applied sequentially. In such a sequential application, the sulindac will have to be applied first followed by the peroxide. Preferably, the applications are made within one hour and most preferably, they are made within about one half hour of each other.

In a preferred embodiment, the methods and pharmaceutical compositions of the present invention are used for the treatment or prevention of neoplasia disorders including the group consisting of acral lentiginous melanoma, actinic keratoses, adenocarcinoma, adenoid cystic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epithelioid, Ewing's sarcoma, fibrolamellar, focal nodular hyperplasia, gastrinoma, germ cell tumors, glioblastoma, glucagonoma, hemangioblastomas, hemangioendothelioma, hemangiomas, hepatic adenoma, hepatic adenomatosis, hepatocellular carcinoma, insulinoma, intraepithelial neoplasia, interepithelial squamous cell neoplasia, invasive squamous cell carcinoma, large cell carcinoma, leiomyosarcoma, lentigo maligna melanomas, leukoplakias, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

In another preferred embodiment, the pharmaceutical compositions of the invention selectively kill all cancers or hyper-proliferative pre-malignant cells. Included in these cell types are cancers arising from viruses or physical agents that would lead to hyper-proliferative states. For example, pox viruses create a hyper-proliferative state similar to a cancer. HPV causes papillomas and cervical polyps (fibroids) that are not malignant but are proliferations that may be affected by the combination.

In a preferred embodiment, a pharmaceutical composition comprises sulindac, sulindac epimers, sulindac metabolites, sulindac derivatives and any combinations thereof, with an ROS-inducing agent. Preferably, the sulindac metabolite comprises sulindac sulfide or sulindac sulfone.

In a preferred embodiment, the ROS-inducing agent is DCA.

In another preferred embodiment, the sulindac comprises R- and S-epimers of sulindac. Preferably, the sulindac is an R-epimer. The R-epimer of sulindac can retain its cancer killing effects. In normal cells, but not cancer cells, the R-epimer of sulindac is not efficiently converted to the sulfide, the active COX inhibitor. Since COX inhibitors produce serious toxicity, it is expected that the R-epimer of sulindac can be a potentially superior therapeutic agent because it would have a lower toxicity profile in normal cells.

Sulindac, unlike its metabolites, is a chiral compound since it contains a methyl sulfoxide moiety, in which there is asymmetry around the sulfur atom. Therefore, the drug sulindac consists of an equal mixture of the R- and S-epimers, and would be a substrate for enzymes that are specific for either epimer. Reduction of either epimer of sulindac, which is a prodrug, will yield sulindac sulfide, which is the active COX inhibitor. Either epimer of sulindac would be advantageous to other compounds if it would not be efficiently converted to a COX inhibitor in normal cells in vivo.

In another preferred embodiment, the ROS-inducing agent oxidizing agent comprises: dichloroacetic acid.

In another preferred embodiment, the ROS-inducing agent is DCA in a concentration is in a range of about 0.001% to 80% by volume.

In another preferred embodiment, the sulindac concentration is in a range from about 0.001% to 100% by volume. In another preferred embodiment, sulindac comprises the R-epimer of sulindac.

In other preferred embodiments, a sulindac gel is 10% sulindac, 15% sulindac, 20% sulindac, 50% sulindac, 100% v/v of sulindac. Preferably, sulindac comprises the R- and/or S-epimer of sulindac.

In another preferred embodiment, a method of treating an abnormal cell and/or preventing a cell from becoming abnormal, and/or abnormal cell growth, comprises administering to an abnormal cell a pharmaceutical composition comprising sulindac, or sulindac metabolites, or sulindac derivatives or combinations thereof, and, an ROS-inducing agent, thereby treating an abnormal cell. Preferably, the sulindac metabolite comprises sulindac sulfide or sulindac sulfone.

In yet another embodiment, a method of treating or preventing cancer, said method comprising administering to a cancer cell a pharmaceutical composition comprising sulindac, or sulindac metabolites, or sulindac derivatives or combinations thereof, and an oxidating agent, thereby treating cancer. Sulindac, sulindac metabolites, sulindac derivatives and an oxidating agent. Preferably, the sulindac metabolite comprises sulindac sulfide or sulindac sulfone. Preferably, sulindac comprises the R-epimer of sulindac, derivatives, metabolites or variants thereof.

Cancer Therapy:

In accordance with the invention tumor target cells are selectively targeted by the compositions. Tumors can be the result of infection by a tumor causing virus or other means.

In another preferred embodiment, abnormal or cancer cells are targeted by the compositions. For example, many malignancies are associated with the presence of foreign DNA, e.g. Bcr-Abl, Bcl-2, HPV.

The invention in general provides a method for treating diseases, such as cancer and diseases which are caused by infectious agents such as viruses, bacteria, intra- and extracellular parasites, insertion elements, fungal infections, etc., which may also cause expression of gene products by a normally unexpressed gene, abnormal expression of a normally expressed gene or expression of an abnormal gene.

The methods of the invention are preferably employed for treatment or prophylaxis against diseases caused by abnormal cell growth and by infectious agents, particularly for treatment of infections as may occur in tissue such as lung, heart, liver, prostate, brain, testes, stomach, intestine, bowel, spinal cord, sinuses, urinary tract or ovaries of a subject.

In another preferred embodiment, the compositions of the invention can be administered in conjunction with chemotherapy. These chemotherapeutic agents can be co-administered, precede, or administered after the compositions. Non-limiting examples of chemotherapeutic agents include, but not limited to: cyclophosphamide (CTX, 25 mg/kg/day, p.o.), taxanes (paclitaxel or docetaxel), busulfan, cisplatin, cyclophosphamide, methotrexate, daunorubicin, doxorubicin, melphalan, cladribine, vincristine, vinblastine, and chlorambucil.

In another preferred embodiment, the pharmaceutical composition inhibits the tumor cell growth in a subject, and the method comprises administering to the subject a pharmaceutical composition comprising a therapeutically effective amount of the composition. Inhibition of tumor cell growth refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

Combination Therapies:

The therapeutic compositions of the present invention may be combined with any other methods generally employed in the treatment of the particular tumor, disease or disorder that the patient exhibits. So long as a particular therapeutic approach is not known to be detrimental to the patient's condition in itself, and does not significantly counteract the instant composition treatment, its combination with the present invention is contemplated.

Therapeutic agents can include, for example, chemotherapeutic agents such as, cyclophosphamide (CTX, 25 mg/kg/ day, p.o.), taxanes (paclitaxel or docetaxel), busulfan, cisplatin, methotrexate, daunorubicin, doxorubicin, melphalan, cladribine, vincristine, vinblastine, chlorambucil, tamoxifen, taxol, etoposide (VP-16), adriamycin, 5-fluorouracil (5FU), camptothecin, actinomycin-D, mitomycin C, cisplatin (CDDP), combretastatin(s) and derivatives and prodrugs thereof.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 $mg/m^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 $mg/m^2$ at 21 day intervals for adriamycin, to 35-50 $mg/m^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

The skilled artisan is directed to "Remington's Pharmaceutical Sciences" 15th Edition, chapter 33, in particular pages 624-652, for non-limiting examples of other chemotherapeutic agents that can be used in combination therapies with the PWM-poly IC-PHA compositions. Some variation in dosage will necessarily occur depending on the condition of the subject being treated. The physician responsible for administration will be able to determine the appropriate dose for the individual subject.

In connection solid tumor treatment, the present invention may be used in combination with classical approaches, such as surgery, radiotherapy, chemotherapy, and the like. The invention therefore provides combined therapies in which the therapeutic compositions are used simultaneously with, before, or after surgery or radiation treatment; or are administered to patients with, before, or after conventional chemotherapeutic, radiotherapeutic or other anti-angiogenic agents, or targeted immunotoxins or coaguligands.

When one or more agents are used in combination with the sulindac-peroxide compositions there is no requirement for the combined results to be additive of the effects observed when each treatment is conducted separately. Although at least additive effects are generally desirable, any increased anti-tumor effect above one of the single therapies would be of benefit. Also, there is no particular requirement for the combined treatment to exhibit synergistic effects, although this is certainly possible and advantageous.

To practice combined anti-tumor therapy, one would simply administer to an animal the composition in combination with another anti-cancer agent in a manner effective to result in their combined anti-tumor actions within the animal. The agents would therefore be provided in amounts effective and for periods of time effective to result in their combined presence within the tumor vasculature and their combined actions in the tumor environment. To achieve this goal, the compositions and other anti-cancer agents may be administered to the animal simultaneously, either in a single composition, or as two distinct compositions using different administration routes.

Alternatively, the composition mediated treatment may precede, or follow, the a second anti-cancer agent treatment by, e.g., intervals ranging from minutes to weeks. In certain embodiments where the anti-cancer agent and the composition are applied separately to the animal, one would ensure that a significant period of time did not expire between the time of each delivery, such that the anti-cancer agent and the composition would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

The general use of combinations of substances in cancer treatment is well known. For example, U.S. Pat. No. 5,710,134 (incorporated herein by reference) discloses components that induce necrosis in tumors in combination with non-toxic substances or "prodrugs". The enzymes set free by necrotic processes cleave the non-toxic "prodrug" into the toxic "drug", which leads to tumor cell death. Also, U.S. Pat. No. 5,747,469 (incorporated herein by reference) discloses the combined use of viral vectors encoding p53 and DNA damaging agents. Any such similar approaches can be used with the present invention.

In some situations, it may even be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the sulindac-oxide composition treatment, and another treatment was intended to prevent micrometastasis or tumor re-growth, such as the administration of an anti-angiogenic agent.

It also is envisioned that more than one administration of either the composition or another anti-cancer agent will be utilized. The composition and anti-cancer agents may be administered interchangeably, on alternate days or weeks; or a sequence of the composition treatment may be given, followed by a sequence of anti-cancer agent therapy. In any event, to achieve tumor regression using a combined therapy, all that is required is to deliver both agents in a combined amount effective to exert an anti-tumor effect, irrespective of the times for administration.

In terms of surgery, any surgical intervention may be practiced in combination with the present invention. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means.

Cytokine therapy also has proven to be an effective partner for combined therapeutic regimens. Various cytokines may be employed in such combined approaches. Examples of cytokines include IL-1α, IL-1β, IL-2, IL-3, IL-4, IL-5, IL-6, IL-7, IL-8, IL-9, IL-10, IL-11, IL-12, IL-13, TGF-β, GM-CSF, M-CSF, G-CSF, TNFα, TNFβ, LAF, TCGF, BCGF, TRF, BAF, BDG, MP, LIF, OSM, TMF, PDGF, IFN-α, IFN-β, IFN-γ. Cytokines are administered according to standard regimens, consistent with clinical indications such as the condition of the patient and relative toxicity of the cytokine. Uteroglobins may also be used to prevent or inhibit metastases (U.S. Pat. No. 5,696,092; incorporated herein by reference).

Effective Amounts

The compositions described above are preferably administered to a subject in an effective amount. A therapeutically effective amount is an amount which is capable of producing a desirable result in a treated animal or cell (for example, to induce apoptosis or impair mitosis in a cell in the animal or a culture). As is well known in the medical and veterinary arts, dosage for any one animal depends on many factors, including the particular animal's size, body surface area, age, the particular composition to be administered, time and route of administration, general health, and other drugs being administered concurrently. It is expected that an appropriate dosage for topical administration of the sulindac in the topical formulation can range from 0.001% to 99.9%. An effective amount for use with a cell in culture will also vary, but can be readily determined empirically (for example, by adding varying concentrations to the cell and selecting the concentration that best produces the desired result). It is expected that an appropriate concentration would be in the range of about 1-5000 μM.

Method for Preventing and Inhibiting Cancer Cell Growth

The invention provides a method for preventing and inhibiting tumor cell growth or increasing the rate of tumor cell apoptosis. The method includes the steps of contacting a tumor cell with a composition, and, optionally a sufficient amount of sulindac-ROS inducing agent compositions to kill or at least retard mitosis in the tumor cell. The method may be used to prevent or inhibit the growth of numerous types of cancerous tumor cells. The compositions have been tested and shown to be effective against different types of tumors such as melanoma, squamous, and breast cancer cells. (See, examples which follow). Sulindac (or related compounds thereof) comprising compositions are expected to be effective against other cancers as well, particularly those derived from epithelial, mesenchymal, and hemopoietic origins. Preferably, sulindac comprises the R-epimer of sulindac, derivatives, metabolites or variants thereof.

Any suitable formulation of sulindac-peroxide can be used in methods of the invention. Typical formulations are topical liposomal formulations of the compositions of varying concentrations. In addition to topical administration, sulindac-peroxide containing formulations can be administered to a subject via injection (e.g., IP, IV, IM, SQ).

In preferred embodiments, administration of sulindac-oxide compositions results in one or more phenotypes of a tumor cell being inhibited. For example, inhibition of tumor growth, reduction of tumor size, inhibition of metastasis, reduction in the number of tumor cells and the like. Each of these phenotypes of a tumor cell can be measured using standard assays, such as for example, imaging, mechanical measurements, in vitro assays and the like.

Formulations

A compound of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, inhalation or infusion techniques.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

The methods and combinations of the present invention provide one or more benefits. Combinations of the present invention may allow for a lower dose of each agent. A benefit of lowering the dose of the compounds, compositions, agents and therapies of the present invention administered to a mammal includes a decrease in the incidence of adverse effects associated with higher dosages.

By lowering the incidence of adverse effects, an improvement in the quality of life of a patient undergoing treatment for cancer is contemplated. Further benefits of lowering the incidence of adverse effects include an improvement in patient compliance, a reduction in the number of clinical visits needed for the treatment of adverse effects, and a reduction in the administration of analgesic agents needed to treat pain associated with the adverse effects.

Alternatively, the methods and combination of the present invention can also maximize the therapeutic effect at higher doses.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

The composition of the invention can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, $18^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. In addition to treatment of cancer with topical formulations of the composition, in other aspects of the invention the composition can be delivered by other methods. For example, the composition can be formulated for parenteral delivery, e.g., for subcutaneous, intravenous, intramuscular, or intratumoral injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions are preferably formulated in a sterilized pyrogen-free form. Compositions of the invention can also be administered in vitro to a cell (for example, to induce apoptosis in a cancer cell in an in vitro culture) by simply adding the composition to the fluid in which the cell is contained.

Depending on the specific conditions being treated, such agents may be formulated and administered systemically or locally. Techniques for formulation and administration may be found in Remington's Pharmaceutical Sciences, $18^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate is a preferred buffer.

The final pH value of the pharmaceutical composition may vary within the physiological compatible range. Necessarily, the final pH value is one not irritating to human skin and preferably such that transdermal transport of the active compound, i.e. sulindac, peroxide, arsenic trioxide is facilitated. Without violating this constraint, the pH may be selected to improve the compound stability and to adjust consistency when required. In one embodiment, the preferred pH value is about 3.0 to about 7.4, more preferably about 3.0 to about 6.5, most preferably from about 3.5 to about 6.0.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Other known transdermal skin penetration enhancers can also be used to facilitate delivery of the composition. Illustrative are sulfoxides such as dimethylsulfoxide (DMSO) and the like; cyclic amides such as 1-dodecylazacycloheptane-2-one (AZONE™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like. Also suitable as skin penetration enhancers are organic acids and esters such as salicyclic acid, methyl salicylate, citric acid, succinic acid, and the like.

Kits and Formulations

The invention also provides a kit for reducing the rate of tumor growth in a subject. The kit of the invention includes a composition comprising sulindac, sulindac derivatives, variants etc, oxides such as hydrogen peroxide, arsenic trioxide etc, and, optionally a pharmaceutically acceptable carrier as well as printed instructions for using the composition to reduce the rate of tumor growth in a subject.

Active components can be present in solid, semi-solid or liquid form. Solid forms include for example, powders, granules and flakes. Semi-solid forms include, for example, gels, creams, gelatins and ointments. These and other active agents embraced by the present invention are known to those of ordinary skill in the art and, in most cases, are commercially available from suppliers such as Compound Solutions, Inc., Escondido, Calif. Information on these and other active and inactive agents embraced by the invention, and their commercial suppliers is available from various trade manuals, most particularly, Remington's Pharmaceutical Sciences, United States Pharmacopoeia (USP), National Formulary (NF), Merck Index, Physician's Desk Reference (PDR) and Chemical Abstracts.

The kits of the invention will also generally contain at least one inactive agent. As used herein, inactive agents are agents which do not provide any therapeutic benefit to the subject to whom they are administered. Instead, inactive agents can function in many other ways such as to provide a base in which the active agent can be dissolved or suspended, to dilute the active agent in order to provide proper doses upon administration, to facilitate the dissolution or suspension of the active agent, or to prevent oxidation of the active agent by removing air bubbles from the final compounded suspension. In some embodiments of the invention, the kits lack an inactive agent, and rather contain two or more active agents.

Base agents such as creams, oils, gels or ointments are suitable for topical or suppository applications. The choice of suitable inactive base agent for use in the kits of the invention will depend upon the active agent to be compounded. Suitable base agents will be known to the ordinary artisan. Alternatively, Remington's Pharmaceutical Sciences, the Physician Desk Reference (PDR) or other manuals as listed above, can be consulted in making this determination.

Examples of inactive base agents or components include, for example, lanolin, hydrophilic ointment, white ointment, yellow ointment, polyethylene glycol ointment, petrolatum, hydrophilic petrolatum, white petrolatum, rose water ointment, squalene, hydrogenated vegetable oil (Type II), ultrasound gel, pluronic lecithin organogel (PLO) gel, cream.

The term "petrolatum" as used herein means petrolatum ointment, petrolatum gel or petrolatum cream, all of which are commercially available. It is well within the realm of the ordinary pharmaceutical artisan to determine which form of petrolatum is most appropriate for a specific kit.

A commercially available ultrasound base is either POLYSONIC™ (ultrasound gel) ultrasound lotion or Aquasonic ultrasound 100 gel manufactured by Parker Laboratories, Inc. (Fairfield, N.J.) or EcoGel 100 or EcoGel 200 manufactured by Eco-Med (Mississauga, Ontario, Canada), the compositions of which may include cetyl alcohol, liquid paraffin, polymer, surfactants, preservatives such as propyl paraben and methyl paraben in bacteriostatic concentration, fragrance, and reverse osmosis water. As used herein, a gel is a base with a higher viscosity than a lotion. The physical characteristics of the POLYSONIC™ (ultrasound gel) ultrasound lotion and the EcoGel 100 include pH range of 6.5-7.0, density of 1.04 g/cm3, viscosity of 35,000 to 70,000 cps and acoustic impedence of 1.60 (105 g/cm2 sec). The physical characteristics of Aquasonic ultrasound 100 gel or EcoGel 200 are similar to those of POLYSONIC™ (ultrasound gel) ultrasound lotion and EcoGel 100 except that their viscosity is 80,000 to 110,000 cps. These lotions and gels are available in a clear, colorless form or in a blue colored form.

Liquid bases are recommended for orally administered pharmaceuticals. In some embodiments of the invention, at least one active agent, will be supplied already co-mingled with an inactive agent. Examples of this include the combination of magnesium hydroxide and aluminum hydroxide (commercially available as MAALOX™ (magnesium hydroxide/aluminum hydroxide)), and diphenhydramine HCl (commercially available as BENADRYL™ (diphenhydramine hydrochloride)). Both MAALOX™ (magnesium hydroxide/aluminum hydroxide) and BENADRYL™ (diphenhydramine hydrochloride) are supplied by their respective manufacturers as a combination of active and inactive agents.

Sterile base solutions are preferred for parenteral (i.e., injection), aerosol (i.e., inhalation) and ophthalmic routes of administration. The administration may, for example, be intravenous, intraperitoneal, intramuscular, intracavity, subcutaneous or transdermal. Preparations for parenteral administration includes sterile aqueous or nonaqueous solutions, suspensions and emulsions. The compounded pharmaceuticals, preferably those intended for parenteral, inhalation or ophthalmic routes of administration, may be prepared and administered in inactive agents which are pharmaceutically-acceptable. As used herein, a pharmaceutically-acceptable carrier means a non-toxic material that does not interfere with the effectiveness of the biological activity of the active agents and that is compatible with the biological systems such of a tissue or organism. The physiologically acceptable carrier must be sterile for in vivo administration. Pharmaceutically acceptable carriers include diluents, fillers, salts, buffers, stabilizers, solubilizers and other materials which are well-known in the art. The characteristics of the carrier will depend on the route of administration. In general, pharmaceutically-acceptable agents or carriers are well-known to those of ordinary skill in the art. In some embodiments, suitable sterile solutions include albuterol and ipratropium inhalation solution; papaverine, phentolamine and prostaglandin injection solution; fentanyl citrate injection solution and cyclosporine ophthalmic drops.

Examples of nonaqueous solvents are propylene glycol, polyethylene glycol, vegetable oil such as olive oil, an injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents, and inert gases and the like. Those of skill in the art can readily determine the various parameters for preparing these alternative pharmaceutical compositions without resort to undue experimentation.

Inactive agents may also include components which function to preserve the integrity of the compounded formulation. This latter category of inactive agents includes, for example, anti-foaming agents. Anti-foaming agents are agents which function to remove unwanted air trapped in a composition, perhaps during mixing or agitation. The use of anti-foaming components is particularly useful in the preparation of pharmaceuticals to be used for ultrasound imaging due to the impedance of signal transmission by air bubbles. Examples of other anti-foaming agents useful in the compositions of the invention include bisphenylhexamethicone, dimethicone, dimethiconol, hexamethyldisiloxane, hexyl alcohol, isopropyl alcohol, petroleum distillates, phenethyl disiloxane, phenyl trimethicone, polysilicone-7, propyl alcohol, silica dimethyl silylate, silica silylate, tetramethyl decynediol and trimethylsiloxysilicate. A preferred anti-foaming agent is simethicone. Simethicone is a mixture of about 90% dimethicone and 10% silicone dioxide (either in weight or in volume). Simethicone is used extensively as an anti-gas agent in pharmaceutical products such as GAS-X™ (simethicone), MAALOX™ (magnesium hydroxide/aluminum hydroxide), MYLANTA™ (aluminum, magnesium simethicone), PHAZYME™ (simethicone), GENAZYME™ (simethicone), and MYLICON™ (simethicone) Drops. Simethicone may be used as an anti-foaming agent in any of the formulations embraced by the invention.

Other inactive agents which can be included in the formulations of the invention include stabilizers such as citric acid, anti-oxidants such as sodium metabisulfite and preservatives such as methyl or propyl paraben.

Another class of inactive agents is suspending agents. Suspending agents are agents which facilitate the suspension and in some cases the dissolution of an active agent in a base. Generally, suspending agents ensure more uniform mixing of active and base components. In order to administer a more uniform dose of a compounded pharmaceutical to a patient, the compounded components must be properly and homogeneously combined. If the active agent is present as a powder, a uniform dispersion is sometimes difficult to achieve using the traditional form of compounding.

A subcategory of suspending agents are solubilizers. Solubilizers are agents which facilitate the dissolution of a solid or, in some cases, a semi-solid agent in a base inactive agent. In some embodiments of the invention, a solid-form active agent may be dissolved in a suspending agent, prior to mixing it with the base agent. Conversely, the suspending agent and the base agent may be prepackaged together, particularly if the concern is ensuring the uniform blending of active agent within the base component rather than the loss of solid (i.e., powdery) active agent. In still other variations, the suspending agent may be premixed with the base inactive agent.

Suitable suspending agents useful in the compositions of the invention include, but are not limited to, glycerin, hexylene glycol, propylene glycol, sorbitol, acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, benzalkonium chloride, benzethonium chloride, cetylpyridinium chloride, docusate sodium, nonoxynol 9, nonoxynol 10, octoxynol 9, polyoxyl 50 stearate, and tyloxapol.

Still other suspending agents include humectants and wetting agents. Humectants are agents which retain moisture. Examples of humectants include but are not limited to glycerin, hexylene glycol, propylene glycol and sorbitol. The amounts of base and non-base inactive agents will also depend upon the particular compounded pharmaceutical to be made. Base agents can be provided in quantities corresponding to final compounded preparations which contain 0.5% to 99.99% of base agent, either in weight or in volume. In preferred embodiments, the final concentration of the base agent is 20%-80%. In even more preferred embodiments, the final concentration of the base agent is 40%-80%.

Generally, the amounts of non-base agents will be sufficient to provide final formulations in which each non-base inactive agent represents 0.01%-50% of the composition. Suspending agents may represent 1%-50% of the final formulation. Preferably, suspending agents will represent 1%-40% and even more preferably, they will represent 5%-30% of the final formulation. Anti-foaming agents may represent 0.01% to 20% of the final formulation. More preferably, anti-foaming agents represent 0.05% to 10% of the final formulation and even more preferably, they represent 0.1% to 5% of the final formulation.

In some preferred embodiments, the single or multiple unit of use kits are designed to yield, after the physical mixing of active and inactive agents, compounded pharmaceutical formulations comprising 0.1%, 5%, 10% to 99.9% or 100% either in weight or in volume of sulindac or variants thereof. Preferably, sulindac comprises the R-epimer of sulindac, derivatives, metabolites or variants thereof.

The kits of the invention will provide each and every component required for preparing a given compounded pharmaceutical in pre-measured quantities. The measuring of each component will be performed using current Good Manufacturing Practices (cGMP, as legislated by the Code of Federal Regulations or CFR), as will the packaging and labeling of each component and the final packaging and labeling of the kit in its entirety. In this way, the kits are standardized and variations from batch to batch will be minimal or non-existent and the precision and accuracy in the measurement of individual components will be improved considerably over the methods currently used by pharmacists. Instructions may be provided as separate from any container, but still contained in the kit. Alternatively, instructions may be located on a container, for example, on an exterior surface or on an interior surface such as a lid.

Both the active and the inactive agents of the kit are provided in containers. Since the kit will contain at least one active and at least one inactive agent, or at least two active agents pre-formulated with inactive agents, the minimum number of containers in a given kit will be two. In preferred embodiments, the maximum number of containers in a kit will be less than or equal to four. The containers may be formed in any size or shape useful for the mixing or transferring of components from one container to another. For example, each container may be in the form of vials, bottles, squeeze bottles, jars, sealed sleeves, envelopes or pouches, tubes or blister packages or any other suitable form provided the container is sealed so as to prevent premature mixing of components. As used herein, a container may also be a compartment or a chamber within a vial, a tube, ajar, or an envelope, or a sleeve, or a blister package or a bottle, provided that the contents of one compartment are not able to associate physically with the contents of another compartment prior to their deliberate mixing by a pharmacist or physician.

The invention intends to provide within a single kit all the necessary components, containers and stirring or mixing elements for preparing a unit of use compounded pharmaceutical without the need for other accessories. The kits of the invention may also contain items such as gloves or spill pads. Individuals skilled in the art can readily modify the choice of container to suit the individual components housed and mixed therein.

In some embodiments of the invention, the final compounded formulation will be provided to the patient in the container originally housing the inactive, or base, compound. In other embodiments, the final compounded formulation will be provided in the container originally housing the active agent. In still other embodiments, all the necessary components for preparing a compounded pharmaceutical are included in one container but are physically separated within such a container. For example, an inactive agent may be contained in the lower part of a container, such as a jar, and may be covered by a plastic, peel-off wrap. The active agent may be housed in this same jar, but secured to the lid of the jar and provided in a pouch or a sleeve. The ability to provide all components together in the smallest packaging arrangement may be preferable in some circumstances. Mixing elements required in the preparation of the compounded pharmaceutical may also be located within the same container, for example, secured to the inside surface of the lid of the container.

In still another embodiment of the invention, active and inactive agents are provided in adjacent compartments of a single housing container, and are mechanically removed from these compartments and into a third compartment. As an example, all the chemical components necessary to prepare a particular compounded pharmaceutical can be present in a single tube, for example, a tube similar to a toothpaste tube having an interior which is divided into separate compartments. Each of these compartments in turn house a base agent or an active agent. Either the base agent or the active agent may be premixed with an anti-foaming agent and/or a suspending agent, as described herein. By applying pressure on the tube as a whole, the components are made to exit their respective compartments. They can then be mixed either in an adjacent or a physically separate compartment. Squeezing or pressing of the outside surface of the tube may be all that is necessary to retrieve the individual components housed within the tube. In yet another embodiment, the contents of both chambers of a container can be pumped out and into a third container. In a related embodiment, it is also envisioned that rather than requiring the contents of each compartment to exit and flow into a third compartment, the components may be separated by a removable sheet or film. Thus, upon removal of such a sheet or film, the contents of the two compartments are in contact and may require only agitation or end-over-end inversion to become completely mixed. This latter embodiment would eliminate the need for a mixing element, and potentially for an exterior package particularly if the instructions are written on the container itself.

According to some aspects of the invention, each container may contain one or more active agents or one or more inactive agents. For example, in some embodiments of the invention, none of the containers may contain both an active and an inactive agent prior to mixing by the pharmacist or physician. However, the invention also provides for kits in which a container may contain an active and at least one inactive agent, such as a base agent, a suspending agent or an anti-foaming agent.

In a preferred embodiment, the active agent is provided premixed with an inactive agent. This applies mainly when sulindac will be commercially available as a solid, for example a powder, and the pre-mixing of the powder with a suspending agent facilitates the compounding by the pharmacist or physician. In yet other embodiments, at least two of the inactive agents may be pre-mixed as provided in the kits of the invention.

In some embodiments, where the active agent is added to the base component, it may be desirable to provide the base component in a container which is only partially full. In preferred embodiments, the container in which the base component is situated is less than 100% full by volume. In other embodiments, the containers are 95%, 90%, 80%, 75%, 70%, 60%, 50%, 40%, 30%, 25%, 20% or less than 20% full by volume. In other embodiments, the active or inactive agents comprise a volume of their respective containers ranging from 100% to greater than 1%, and every integer there between. In preferred embodiments, the inactive agent occupies a volume of the second container which is less than or equal to the volume of the second container minus the volume of the active agent.

As used according to the invention, the active and inactive agents are physically combined by a pharmacist to produce a compounded pharmaceutical. The components of the kit can be combined by gentle agitation, shaking, stiffing, folding or end-over-end inversion of the first or second container. In some instances, the proper mixing of the active and inactive agents may be accomplished simply by adding one to the other, followed by sealing and agitation of the container. This is especially the case if the components are both liquids or both semi-solids. In other instances, it may be necessary to stir the components together with a mixing element. Mixing elements are well known to a person of ordinary skill in the pharmaceutical arts and may include for example, centrifuges, a mixing rod such as a glass rod, a spoon, a spatula or a dipstick. Where required, the mixing element is provided in the kit. The presence of a mixing element will vary depending on the compounded pharmaceutical formulation to be made with the components of a kit.

The final compounded pharmaceutical may be formulated into preparations in solid, semi-solid, liquid or gaseous forms such as tablets, capsules, powders, granules, ointments, solutions, suppositories, inhalants and injections, and usual ways for oral, parenteral or surgical administration. The invention also embraces locally administering the compounded pharmaceuticals of the invention such as, for example, as implants. These formulations may be intended for oral, topical, mucosal, parenteral (e.g., injectable), rectal or vaginal administration. In preferred embodiments, the final compounded formulations may be self-administered.

The kits of the invention may also contain a package which may be compartmentalized to receive in close confinement two or more containers of the invention. In some embodiments, the package may be box-like, being made of a moderately rigid material such as cardboard or reinforced paper. In other embodiments, the package may be a bag. In still other embodiments, as described herein, there is no external packaging and all containers may be incorporated into one of the containers housing either an active or an inactive agent. This latter embodiment can be accomplished by securing containers such as pouches, sleeves or sacs, containing either active or inactive agents, as well as any mixing elements required for the compounding, to the interior of the lid of the main container. An individual skilled in the art can readily modify the package to suit the individual needs of each kit and each use. The kits of the invention further contain instructions for the proper use of the components found therein.

The kits of the invention are intended for use in the treatment or prevention of a number of disorders in a variety of subjects including humans, dogs, cats, horses, fish, pigs, cows, sheep, deer, zoo animals and laboratory animals (e.g., mice, rats, rabbits, monkeys, etc.). The invention intends to embrace unit of use kits containing the above preparations.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Example serves to illustrate selected embodiments of the invention. It will be appreciated that variations in proportions and alternatives in elements of the components shown will be apparent to those skilled in the art and are within the scope of embodiments of the present invention.

Example 1

Combination of Sulindac and Sodium Dichloroacetate Selectively Kills Cancer Cells by a Mechanism Involving Reactive Oxygen Species Materials and Methods
Materials:
Sulindac, N-acetylcysteine, Tiron were purchased from Sigma (St. Louis, Mo.). DCA sodium salt was obtained from Acros Organics (Geel, Belgium). H2DCFDA and JC-1 were obtained from Molecular Probes (Eugene, Oreg.). MTS assay and Deadend Tunel Kit was obtained from Promega (Madison, Wis.). All cell culture media, fetal bovine serum, and other supplements such as penicillin/streptomycin, glutamine, etc. were purchased from American Type Culture Collection (ATCC; Rockville, Md.).
Cell Culture:
A non small cell lung carcinoma cell line (NSCLC), A549 and a skin carcinoma cell line, SCC25 were purchased from ATCC (Rockville, Md.) and maintained in F12-K medium supplemented with 10% fetal bovine serum, 1× penicillin/streptomycin and 1× glutamine in a humidified, 5% $CO_2$ incubator at 37° C. The normal human lung (MRC-5) and keratinocytes were obtained from ATCC (Rockville, Md.) and maintained in the recommended culture medium. Early passage, non-immortalized cells were used for the experiments.
Cell Viability Assay:
The A549 lung and SCC25 skin carcinoma cell lines were plated at $3\times10^3$ and $7.5\times10^3$ cells per well in a 96-well plate. The cells were grown for 18-20 hours, the medium discarded in aseptic conditions and replaced with fresh culture medium containing the indicated drug combinations. The plates were incubated for 48 hours at 37° C. in a 5% $CO_2$ incubator. The culture medium was discarded and the cells were thoroughly rinsed in 1×PBS. Cell viability was determined by using the CellTiter 96 Aqueous One Cell Proliferation Assay (Promega) according to the manufacturer's instructions. The assay utilizes a novel tetrazolium compound that gets converted into a water-soluble formazan by the action of cellular dehydrogenases present in the metabolically active cells. The formazan was quantitated by measuring the absorbance at 490 nm using a colorimetric microtiter plate reader (SpectraMax Plus; Molecular Devices). Background absorbance was subtracted from each sample and plotted.

Intracellular Measurement of ROS:

Following the treatment, cells were incubated with 50 µM of dichlorodihydrofluorescein diacetate ($H_2DCFDA$, Molecular Probes) in indicator fee medium for 30 min at 37° C. Cells were rinsed with PBS and ROS levels were visualized by fluorescence microscopy.

JC-1 Staining to Monitor Mitochondrial Membrane Potential:

Mitochondrial membrane potential was determined using the JC-1 dye from Invitrogen (Carlsbad, Calif.). Disruption and subsequent loss of mitochondrial membrane potential leads to increased green fluorescence in the cytosol and a corresponding decrease in the mitochondrial red fluorescence. Thus changes in mitochondrial membrane potential were determined by following the red to green staining shift using and FITC filter (Zeiss inverted microscope-Axiovert 40 CFL). The images were capture using the Q capture software and processed in Adobe photoshop.

TUNEL (Terminal Deoxynucleotidyl Transferase Mediated Nick End Labeling Assay) Staining to Monitor Cells Undergoing Apoptosis:

TUNEL assay was performed in 96 well plates using DeadEnd colorimetric tunnel assay kit following the manufacturer's protocol. In brief, after treatment, the cells were fixed with formalin and permeablized with 0.2% Triton-X-100 in PBS. Cells were incubated with recombinant terminal deoxynucleotidyl transferase (TdT) and biotinylated nucleotides. Endogenous peroxidases were blocked with 0.3% $H_2O_2$ prior to the incubation with Horseradish peroxidase-streptavidin (HRP-Streptavidin), that binds to the biotinylated nucleotides incorporated into the nicked ends present in cells undergoing apoptosis. HRP-Streptavidin labeled cells are detected by hydrogen peroxide and diaminobenzidine (DAB). Cells that show dark brown nuclear staining are indicative of apoptosis.

Cytotoxicity Assays in Presence of ROS Scavengers:

Cells were co-treated with 2 mM N-acetylcysteine (NAC) and 2 mM 4,5-dihydroxy-1,3 benzenedisulfonic acid disodium salt) along with sulindac and DCA for 48 h at 37° C. Cell viability was monitored by MTS assay as mentioned above.

Figure 1B:
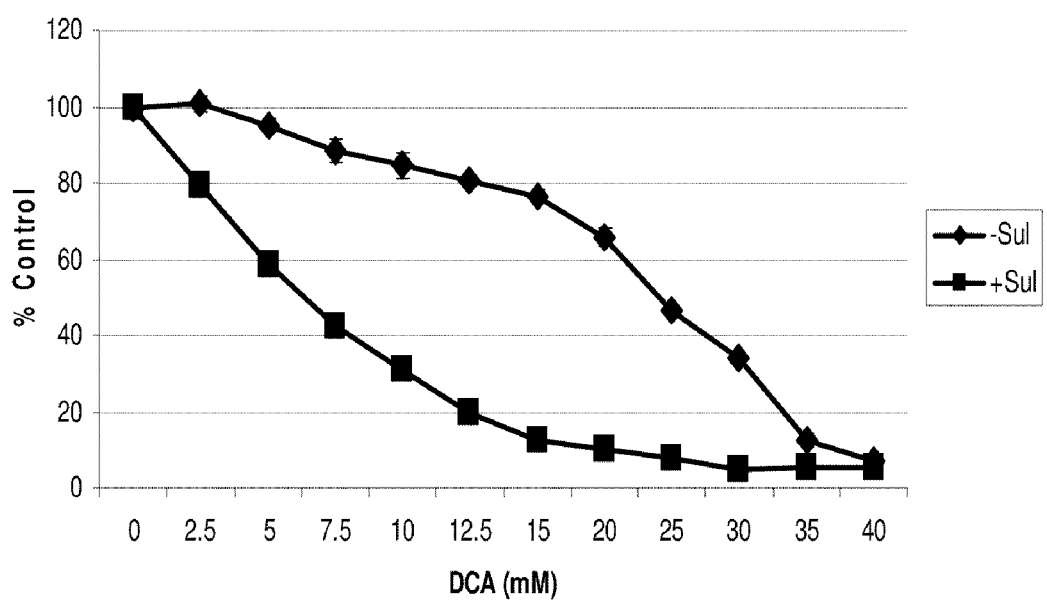
Figure 1C:
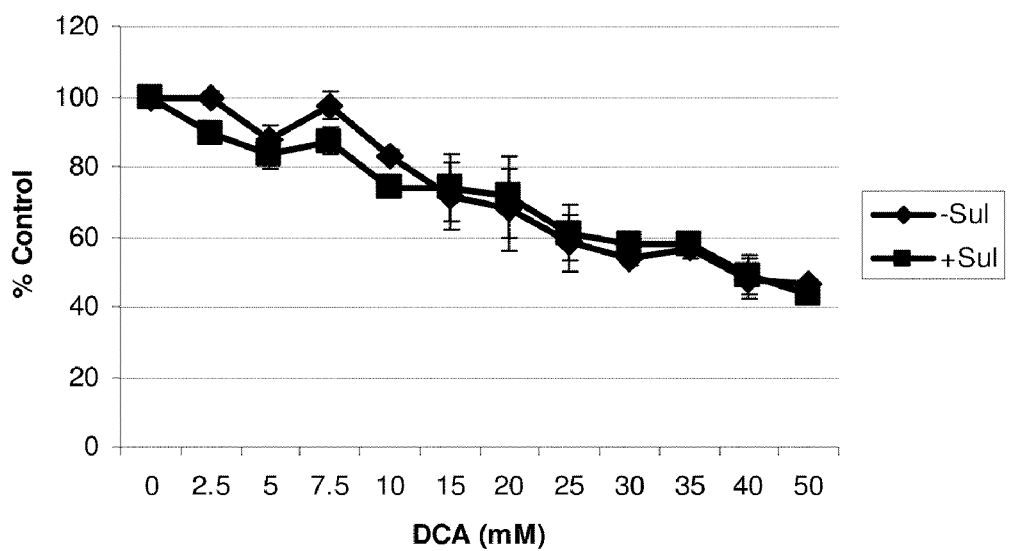
Figure 1D:
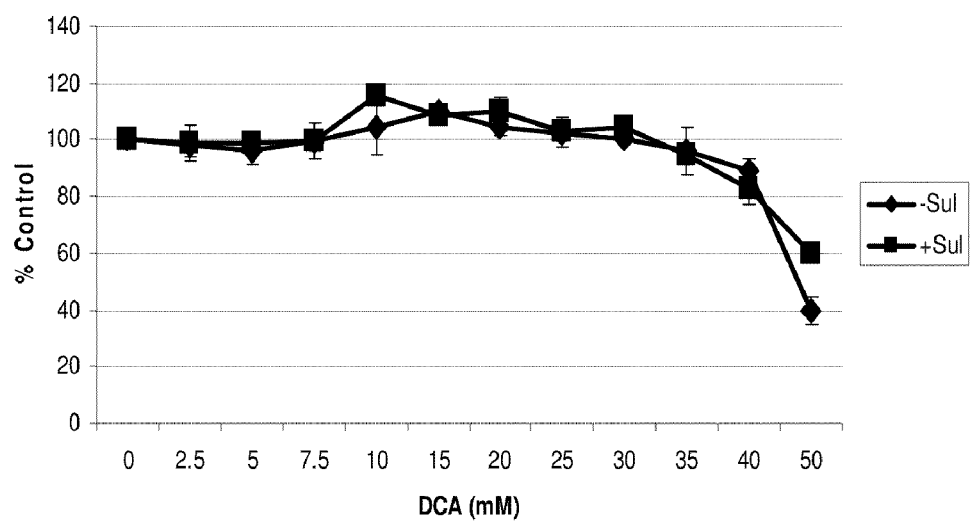

Results:

Sulindac and DCA cause enhanced killing of lung and skin cancer cells For these initial studies the combination of sulindac and dichloroacetate was tested on A549 lung carcinoma and SCC25 skin squamous carcinoma cells. For these experiments the cells were incubated with each compound alone or the combination for 48 hours before assaying for viability (see Methods). A sulindac dose response curve under these conditions indicated that A549 and SCC25 cells can tolerate a maximum concentration 500 µM and 100 µM of sulindac, respectively, without exhibiting any significant killing. DCA, when added, was used at concentrations from 0-40 mM. As shown in FIGS. 1A and 1B, DCA alone is toxic to A549 cells (lung cancer) above 20 mM, but in the presence of sulindac there is enhanced killing (about 3 fold) of these cells between 15-30 mM DCA. In the case of the SCC25 cells loss of cell viability with DCA alone was seen at concentrations below 10 mM (FIG. 1B). However, in the presence of sulindac there was also a striking loss of viability. As shown in FIG. 1B, concentrations of DCA between 5-10 mM show a 3 fold increase in cell death. For most studies DCA concentrations of 15 mM and 10 mM were used with the A549 and SCC25 cells, respectively. Our previous studies had shown that the combination of sulindac and an oxidizing agent was selective for cancer cells and did not enhance the killing of normal cells. Similar results have been obtained with the combination of sulindac and DCA as seen in FIGS. 1C and 1D where the effect of sulindac and DCA on the viability of normal lung (FIG. 1C) and skin keratinocytes, (FIG. 1D) is shown. There was no enhanced killing observed.

Figure 2A:
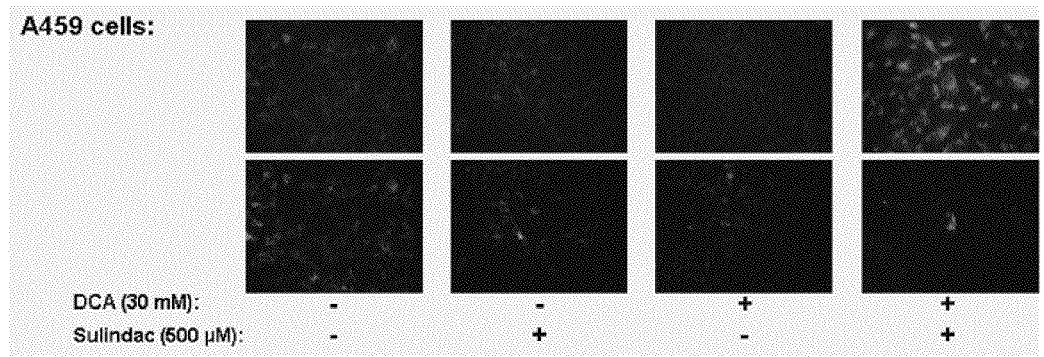
FIGS. 2A and 2B show a significant increase in intracellular ROS levels in lung and skin carcinoma cells during sulindac and DCA combination treatment. Top panels (FIG. 2A) illustrate the results for A549 lung carcinoma cells while the bottom panels (FIG. 2B) depict the results for SCC25 skin carcinoma cells. The extent of intracellular ROS levels are illustrated as intensity of green fluorescence observed in cells treated with (1,5) no drugs, (2,6) sulindac alone, (3,7) DCA alone, and (4,8) sulindac and DCA combination treatment. The cells were treated with the indicated drugs and processed for fluorescent microscopy as described in the Materials and Methods. Several independent fields were photomicrographed and representative fields for each condition are shown. A marked increase in green fluorescence was only observed during sulindac and DCA combination treatment (4, 8) in both lung and skin carcinoma cells.
Figure 2B:
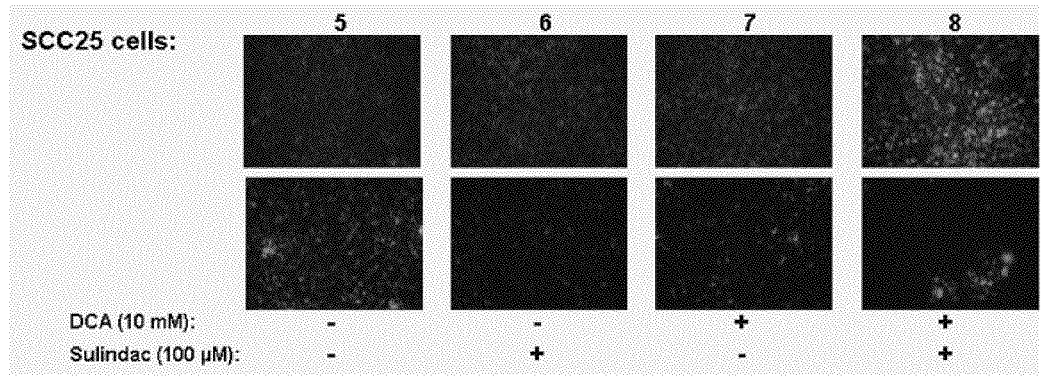
Figure 3A:
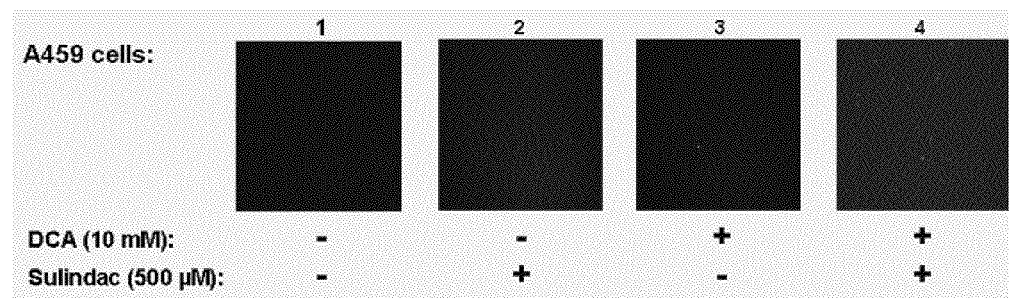
FIGS. 3A and 3B show that a disruption of mitochondrial membrane potential was observed during sulindac and DCA combination treatment as monitored by JC-1 staining. Top panels (A) illustrate the results for A549 lung carcinoma cells while the bottom panels (B) depict the results for SCC25 skin carcinoma cells. Upper series in (A) and (B) illustrate green fluorescence while the lower series in (A) and (B) depict the red fluorescence. Mitochondrial membrane potential loss was detected by a change in JC-1 distribution i.e., a decrease in red fluorescence with a concomitant increase in green fluorescence. The experimental conditions for JC-1 staining and fluorescent microscopy are explained in detail under Materials and Methods and the drug treatment regimens are depicted below the panels. (1,5) untreated cells, (2,6) cells treated with sulindac, (3,7) cells treated with DCA, and (4,8) cells treated with sulindac and DCA. Several independent fields were photomicrographed and representative fields for each condition are shown. A marked increase in green fluorescence with a concomitant decrease in red fluorescence was only observed during sulindac and DCA combination treatment (4,8) in both lung and skin carcinoma cells.
Figure 3B:
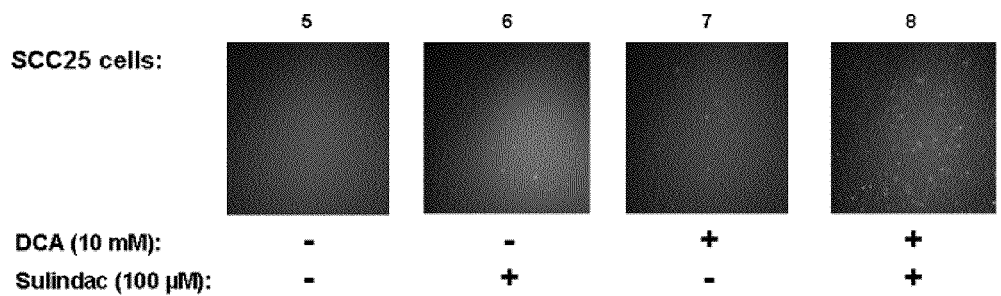

The synergistic effect on viability observed with sulindac and dichloroacetate with both A549 and SCC25 cell lines was strikingly similar to using the combination of sulindac and TBHP. It appeared that ROS production was important in the previous studies so the production of ROS, using the indicator dye $H_2DCFDA$ (see Methods), was also determined in the cancer cell lines exposed to sulindac and DCA. The results are summarized in FIGS. 2A and 2B. FIG. 2A shows the results with A549 cells. It is clearly evident from the results depicted in FIGS. 2A and 2B that the untreated cells (no drug, panel 1), or cells treated with sulindac alone (panel 2), or DCA alone (panel 3), showed only a few positively stained cells. However, when the cells were exposed to both sulindac and DCA (panel 4), a large increase in positively stained cells for ROS (green fluorescence) were present, showing that the presence of both sulindac and DCA results in the generation of significant levels of ROS. As shown in FIG. 2B similar results were seen with the SCC25 cells. With the SCC25 cells DCA and sulindac alone showed a low, but significant increase in ROS producing cells, compared to no drug (FIG. 2B, panel 5-7), but the large increase in ROS production was again observed when both drugs were added (FIG. 2B, panel 8). It appears from these results and earlier studies that ROS production may be a common feature in the enhanced killing of cancer cells when sulindac is used in combination with other compounds that generate ROS. If ROS production is involved in the sulindac effect it was hypothesized that the production of ROS by the drug combination would affect mitochondrial function and result in a loss of mitochondrial membrane potential. In order to determine whether sulindac in combination altered mitochondrial function, mitochondrial membrane potential was measured using JC-1 staining as described in Methods. A typical result is summarized in FIGS. 3A, 3B. Both A549 and SCC25 cells were exposed to sulindac and DCA either alone or in combination for 48 hrs and stained with JC-1 in order to monitor the mitochondrial membrane potential. FIG. 3A shows the results with the A549 cell line. In the absence of any drug, the mitochondria were intact and maintained their membrane potential as indicated by bright red fluorescence (panel 1, bottom), with little green fluorescence (panel 1, top). In presence of sulindac alone (panel 2, top) or DCA alone (panel 3, top) there is a slight increase in green fluorescence, and slight decrease of red fluorescence (panels 2 and 3, bottom), indicating some loss of mitochondrial membrane potential. However, when both sulindac and DCA were present there is a large loss of mitochondrial membrane potential as evidenced by a significant decrease in red fluorescence (FIG. 3A, 3B, panel 4 bottom) and concomitant large increase in the green fluorescence (FIG. 3A, 3B, panel 4, top). The same pattern was observed when several independent fields were analyzed by fluorescent microscopy. FIG. 3B shows similar results with the SCC25 cells. Once again a significant loss of mitochondrial membrane potential was only seen when the cells were exposed to both sulindac and DCA (FIG. 3B, panel 4).

Figure 4A:
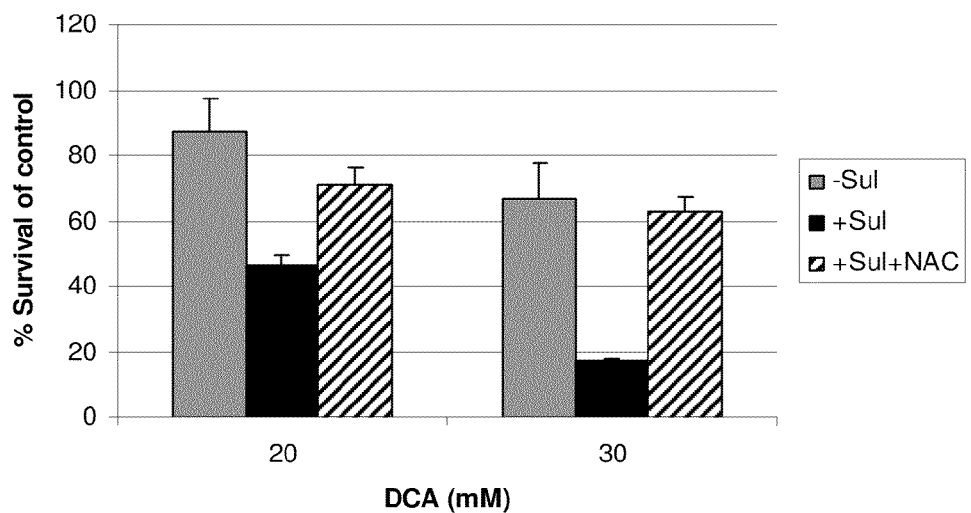
FIGS. 4A-4B show that cancer cell specific cytotoxic effect elicited due to sulindac and DCA combination treatment is reversed by ROS scavengers. The A549 lung and SCC25 skin carcinoma cells were treated with the indicated concentrations of DCA in the absence (grey bar) or presence of sulindac (black bar) or presence of sulindac and N-acetylcysteine (striped bar) for 48 hours. The cell viability was monitored by MTS assay as mentioned in the Materials and Methods. The cell viability is expressed as % of control (cells not treated with sulindac). Error bars are standard error of the mean (SEM) expressed as % of the mean value of quadruplicates from a representative experiment. Inhibition of cancer cell growth occurred in a dose dependent manner during combination treatment of DCA and sulindac (black bars) in both A549 (FIG. 4A) and SCC25 cells (FIG. 4B). However, this cytotoxic effect was eliminated to a considerable extent when N-acetylcysteine was included during this combination treatment.
Figure 4B:
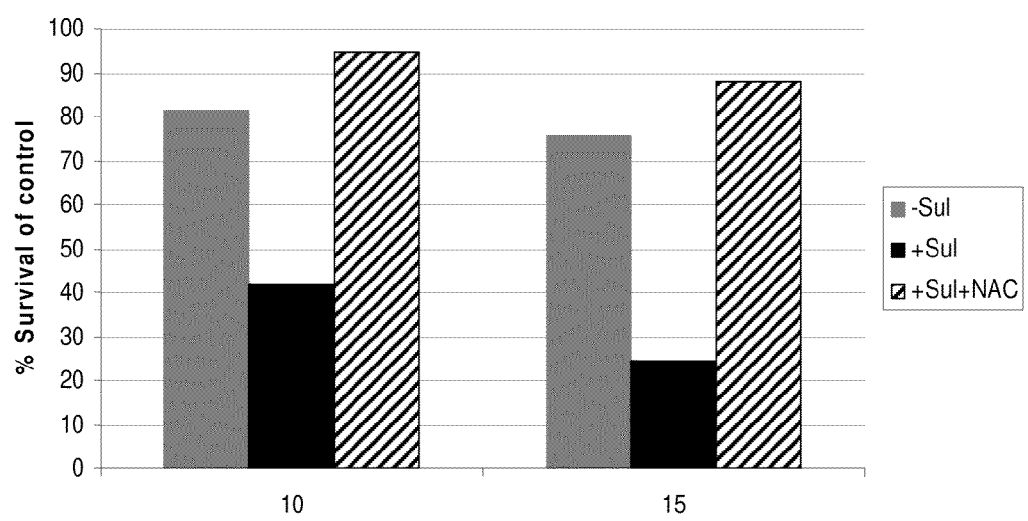

To provide more direct evidence that ROS are involved in the enhanced killing of the cancer cells by sulindac and DCA, two ROS scavengers, N-acetylcysteine (NAC) and Tiron (see Methods) were used. The results using NAC are shown in FIG. 4. FIG. 4A, shows that at both 20 and 30 mM DCA, the enhanced killing of A549 cells in the presence of sulindac, is largely prevented if NAC (2 mM) is present during the 48 hour incubations. Very similar results are seen with SCC25 cells as shown in FIG. 4B. Similar results were obtained with both A549 and SCC25 cell lines when Tiron was used in place of NAC. These results indicated that the enhanced killing of the cancer cell lines using the combination of sulindac and DCA involve ROS production and mitochondrial dysfunction, which suggest that the observed cell death is via apoptosis. Sulindac and DCA killing of cancer cells involves apoptotic death.

Figure 5A:
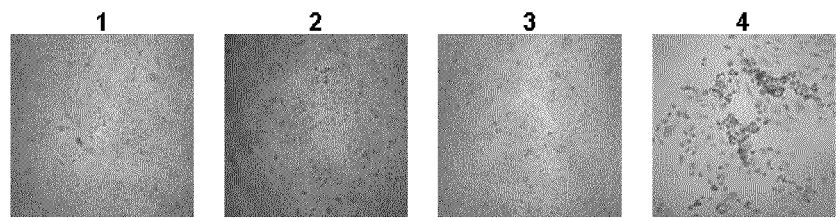
FIGS. 5A-5B show that apoptosis induction was observed during sulindac and DCA combination treatment as revealed by TUNEL staining. Top panels (FIG. 5A) illustrate the results for A549 lung carcinoma cells while the bottom panels (FIG. 5B) depict the results for SCC25 skin carcinoma cells. The extent of cells undergoing apoptosis was monitored by TUNEL staining of cells treated with (1,5) no drugs, (2,6) sulindac alone, (3,7) DCA alone, and (4,8) sulindac and DCA. The cells were treated with the indicated drugs as mentioned in the panels, subjected to TUNEL staining and processed for fluorescent microscopy as described in the Materials and Methods. Several independent fields were photomicrographed and representative fields for each condition are shown. HRP-stained (brown color)-TUNEL positive cells were only observed during sulindac and DCA combination treatment (4, 8) in both lung and skin carcinoma cells.
Figure 5B:
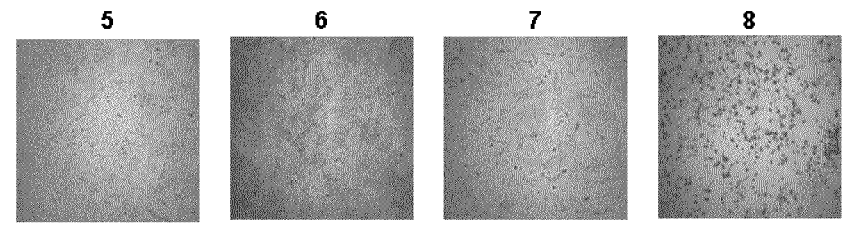

To determine whether killing of the cancer cells by the combination of sulindac and/or its derivatives with DCA, mediated by ROS, involved an apoptotic death, TUNEL staining was performed to measure apoptosis (see Methods). Multiple replicates were tested for sulindac and DCA alone or in combination for the TUNEL staining experiments. A typical result is illustrated in FIGS. 5A, 5B, where the top panels ('1-4) represent the results with the A549 cells and the bottom panels (5-8) depict the results with the SCC25 cells. When the cells were treated with no drug, sulindac alone, or DCA alone (panels 1-3 and 5-7), only a few TUNEL-positive cells were observed. However, when the cells were exposed to both sulindac and DCA, there was a large increase in TUNEL-positive apoptotic cells (panels 4 and 8), indicating a large induction of apoptosis. To verify the TUNEL results, a more sensitive PCR-based DNA laddering assay was also used to monitor apoptosis (see Methods). The results clearly showed the presence of an enriched strong nucleosomal ladder only when both sulindac and DCA were used in combination.

Discussion

Treatment of cancer cells with sulindac renders cancer cells, but not normal cells, more sensitive to oxidative stress. In these experiments the cells were pre-incubated with sulindac for 24-48 hours and then removed the sulindac before the cells were exposed to either TBHP or $H_2O_2$ for 2 hours. These experiments showed that sulindac pretreatment made the cancer cells much more sensitive to the oxidizing agent. It seemed reasonable, based on these results, that sulindac in combination with any compound that produced ROS in cells would result in selective enhanced killing of cancer, but not normal cells. In fact with normal cells we have shown that sulindac protects lung normal cells against oxidative damage and this drug can also protect cardiac cells against oxidative damage caused by ischemia/reperfusion by a preconditioning mechanism.

To our knowledge there are now 4 compounds, in addition to oxidizing agents and DCA that show enhanced cancer killing in the presence of sulindac. These are arsenic trioxide, bortezomib, difluormethylornithine (DMFO), and suberoylanilide hydroxamic acid. Although their targets within the cell are known, but quite different, it is quite likely that they all, directly or indirectly affect mitochondrial function and cause cell death through a mechanism that involves ROS production. In fact, ROS production in cells has been demonstrated with all of the compounds except DFMO. Without wishing to be bound by theory, certain drugs, or drug combination, that selectively kill cancer and not normal cells, the mechanism of killing could involve mitochondrial dysfunction.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method for treating a precancerous or cancerous lesion, the method comprising the steps of (a) administering a non-racemic form of sulindac to the lesion, wherein the non-racemic form of sulindac is selected from the group consisting of R-sulindac and S-sulindac; and (b) administering an oxidizing agent to the lesion, wherein the amount of the oxidizing agent is by itself insufficient to treat the lesion.

2. The method of claim 1, wherein the non-racemic form of sulindac is R-sulindac.

3. The method of claim 1, wherein the non-racemic form of sulindac is S-sulindac.

4. A method for treating a precancerous or cancerous lesion, the method comprising the steps of (a) administering a non-racemic form of sulindac to the lesion, wherein the non-racemic form of sulindac is selected from the group consisting of R-sulindac and S-sulindac; and (b) administering an agent that induces the generation of reactive oxygen species in a cell to the lesion, wherein the amount of the agent that induces the generation of reactive oxygen species administered to the lesion is by itself insufficient to treat the lesion, and wherein the agent that induces the generation of reactive oxygen species in a cell is a peroxide.

* * * * *